US00PP25141P3

(12) United States Plant Patent
Danziger

(10) Patent No.: US PP25,141 P3
(45) Date of Patent: Dec. 2, 2014

(54) *LOBULARIA* PLANT NAMED 'DLOBU22'

(50) Latin Name: *Lobularia maritima*
Varietal Denomination: DLOBU22

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 0 days.

(21) Appl. No.: 13/986,068

(22) Filed: Mar. 27, 2013

(65) Prior Publication Data

US 2014/0298551 P1 Oct. 2, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP21,594 P2 * 12/2010 Wicki ..... Plt./263.1

* cited by examiner

*Primary Examiner* — June Hwu
*Assistant Examiner* — Keith Robinson
(74) *Attorney, Agent, or Firm* — Cassandra Bright

(57) ABSTRACT

A new and distinct *Lobularia* cultivar named 'DLOBU22' is disclosed, characterized by fragrant flowers and along blooming period. The new variety produces a strong, compact, dense and semi-trailing plant, and has a good tolerance of high temperatures. The new variety is a *Lobularia*, normally produced as an outdoor garden or container plant.

2 Drawing Sheets

Figure 1:
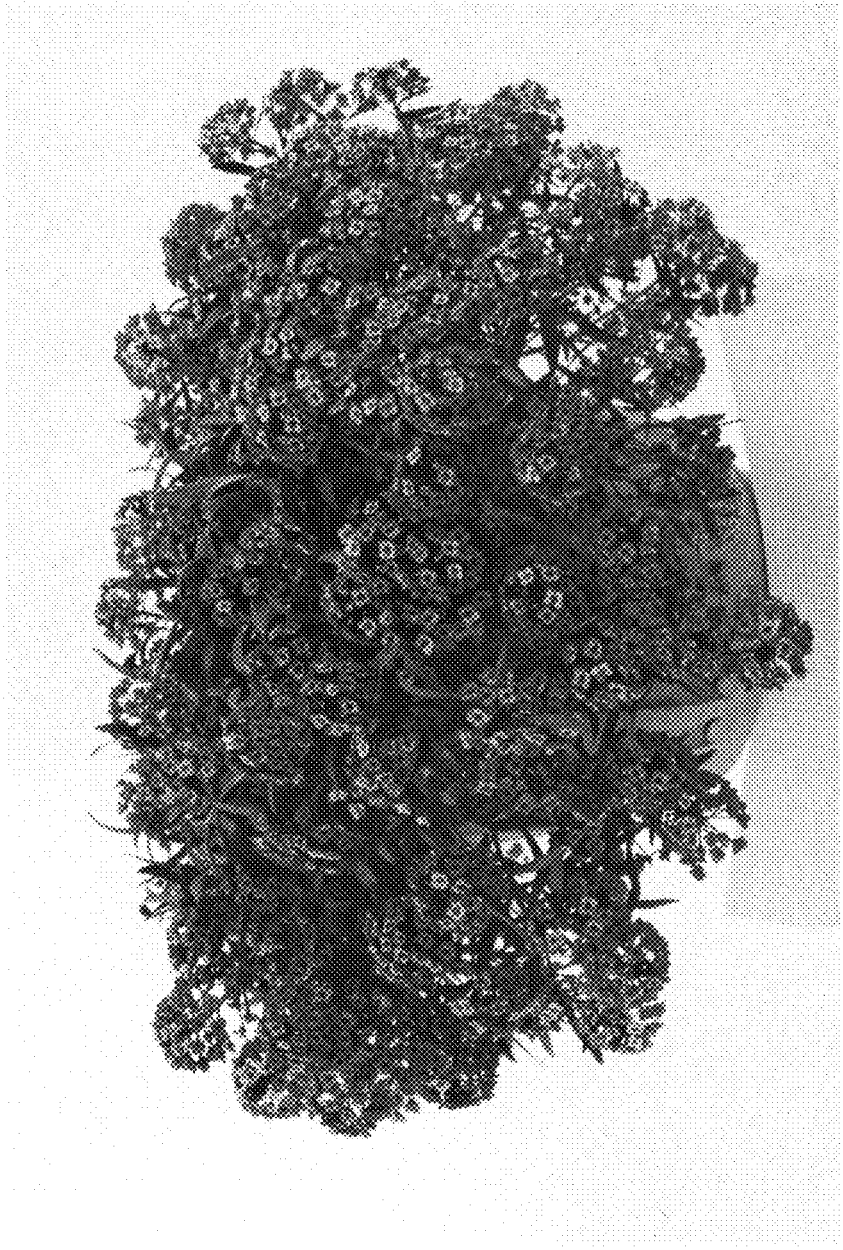

Latin name of the genus and species: *Lobularia maritima*.
Variety denomination: 'DLOBU22'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The open pollination resulting in this new variety was made during February of 2011.

The seed parent is the unpatented, proprietary seedling variety referred to as *Lobularia maritima* 'AY-10-176' The pollen parent is unknown as it was an open pollination breeding program. The new variety was discovered in November of 2011 by the inventor in a group of seedlings resulting from the 2011 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during November of 2011 and has shown that the unique features of this cultivar are stable and reproduced true to type in successive generations.

SUMMARY OF THE INVENTION

The cultivar 'DLOBU22' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBU22' These characteristics in combination distinguish 'DLOBU22' as a new and distinct Lobularia cultivar:

1. Semi-trailing, compact and dense habit.
2. Long flowering period.
3. Freely branching and strong plant structure.
4. Fragrant flowers.
5. Good tolerance to high temperatures.

Plants of the new cultivar 'DLOBU22' are similar to plants of the seed parent, *Lobularia maritima* 'AY-10-176' in most horticultural characteristics, however, plants of the new cultivar 'DLOBU22' produce lavender flowers compared to the white flowers of the seed parent 'AY-10-176'. 'DLOBU22' is more floriferous and longer flowering than seed parent 'AY-10-176'. Additionally 'DLOBU22' produces a bushier, more compact, less trailing plant habit than seed parent 'AY-10-176'.

COMMERCIAL COMPARISON

Plants of the new cultivar 'DLOBU22' are comparable to the variety *Lobularia* 'Inlbublupr' (U.S. Plant Pat. No. 24,516), patent pending, application number undisclosed. The two *Lobularia* varieties are similar in most horticultural characteristics; however, the new variety 'DLOBU22' differs in producing a more compact and dense plant than comparator 'Inlbublupr' (U.S. Plant Pat. No. 24,516). Also 'DLOBU22' has wider and shorter leaves, as well as darker flowers than those of comparator 'Inlbublupr' (U.S. Plant Pat. No. 24,516). Additionally, plants of 'DLOBU22' are not sterile like those of the comparator 'Inlbublupr' (U.S. Plant Pat. No. 24,516).

BRIEF DESCRIPTION OF THE PHOTOGRAPHS

The accompanying photograph in FIG. 1 illustrates in full color a typical plant of 'DLOBU22' grown in a greenhouse, in a 13 cm pot. Age of the plant photographed is approximately 8 weeks from a sticking.

Figure 2:
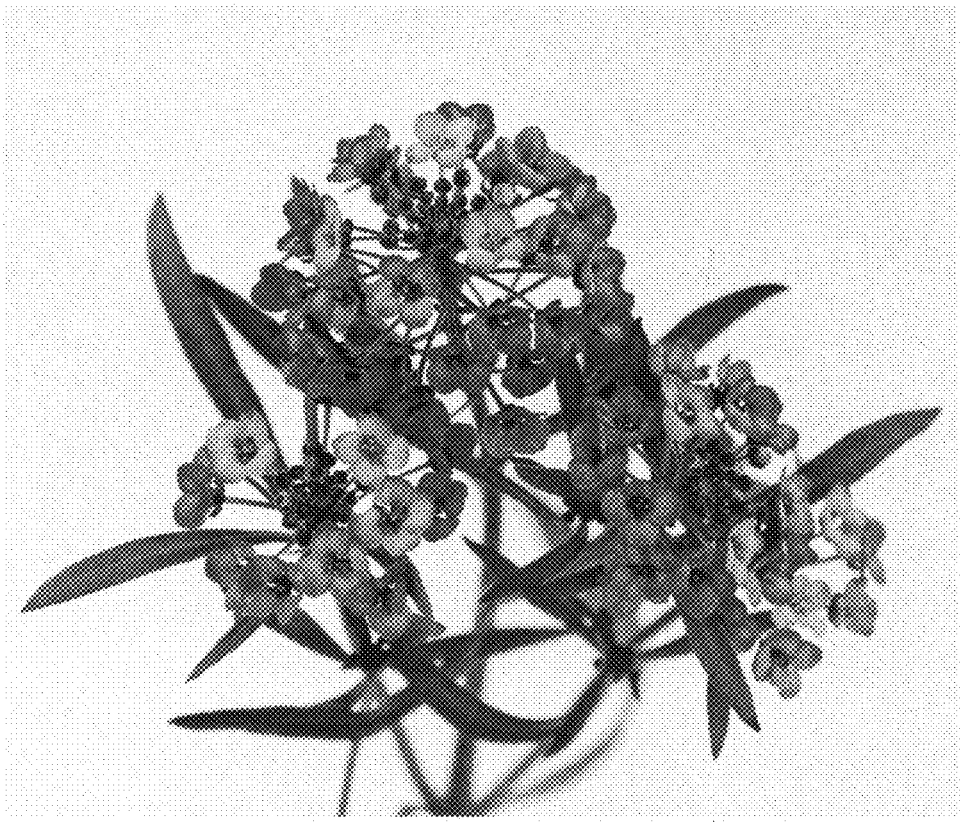

FIG. 2 illustrates in full color a close up of a typical bloom of 'DLOBU22'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DLOBU22' plants grown in a greenhouse during Autumn to Spring in Moshav Mishmar Hashiva, Israel. The growing temperature ranged from 18° C. to 30° C. during the day and from 9° C. to 16° C. during the night. General light conditions are high light levels of 60,000 to 90,000 lux. Measurements and numerical values represent averages of typical plant types.

Botanical classification: *Lobularia maritima* 'DLOBU22'.

PROPAGATION

Typical propagation material: Cuttings.
Time to rooting: 14 to 20 days at approximately 16° C.
Root description: Thin, fibrous, freely branching. Near White group RHS 155C in color.

PLANT

Age of plant described: Approximately 8 weeks.
Growth habit: Compact (Semi trailing and dense).
Height: Approximately 13 cm.
Plant spread: Approximately 30 cm. (radius).
Growth rate: Medium.
Branching characteristics: Freely Branching.
Approximate quantity of lateral branches: Approximately 10 primary lateral branches and numerous secondary and tertiary lateral branches.
Length of lateral branches: Approximately 27 cm.
Diameter of lateral branches: Approximately 0.3 cm.
Texture of lateral branches: Slightly Pubescent.
Lateral branch shape: Hexagonal in cross section.
Lateral branch strength: Strong, flexible.
Lateral branch color: Approximately Yellow-green group RHS 144A.
Internode length: 1-2.5 cm (average).
Number of leaves per lateral branch: Average 8 (per branch).

FOLIAGE

Leaf:
- *Arrangement*.—Alternate.
- *Shape of blade*.—Narrow-elliptical.
- *Average length*.—Approximately 4 cm. ((Mature foliage — 6-7 cm).
- *Average width*.—Approximately 0.8 cm. ((Mature foliage — 1.2 cm).
- *Apex*.—Acute.
- *Base*.—Cuneate.
- *Attachment*.—Sessile.
- *Margin*.—Entire.
- *Texture of top surface*.—Slightly Pubescent.
- *Texture of bottom surface*.—Slightly Pubescent.
- *Leaf internode length*.—None.
- *Color*.—Young foliage upper side: Near Green group RHS 137B. Young foliage under side: Near Green group RHS 137C. Mature foliage upper side: Near Green group RHS 137B. Mature foliage under side: Near Green group RHS 137C.
- *Venation*.—Pinnate and indistinguishable from foliage.

Petiole: Not present.

FLOWER

Bloom period:
- *Natural season*.—Long lasting flowering period. From March through December.
- *In commercial production, flowering begins from a rooted cutting in*.—Approximately 4 weeks.

Inflorescence:
- *Arrangement*.—Panicle.
- *Height*.—Approximately 1.1-1.8 cm.
- *Width*.—Approximately 2.5 cm.
- *Quantity of flowers per inflorescence*.—Approximately 70.

Bud:
- *Bud shape*.—Globose spherical.
- *Bud length*.—Approximately 2 mm.
- *Bud diameter*.—Approximately 1.5 mm.
- *Bud color*.—Near Green group RHS 143A.
- *Rate of opening*.—Individual flowers: Fully open approximately 3 days from the bud stage.

Individual flower:
- *Type of individual flowers*.—Single flower.
- *Shape*.—Cruciform.
- *Quantity of flowers and buds per plant*.—Approximately 80 flowers and buds per inflorescence — more than 2000 flowers per plant.
- *Diameter of entire flower*.—Approximately 0.6 cm.
- *Depth of flower*.—Approximately less than 1 mm.
- *Flower longevity on plant*.—Approximately 5 days.
- *Persistent or self-cleaning*.—Self-cleaning.
- *Fragrance*.—Sweet, honey like.

Petals:
- *Length of petal*.—Approximately 3.5 mm.
- *Width of petal*.—Approximately 3 mm.
- *Apex*.—Rounded.
- *Base*.—Reniform.
- *Shape of petal*.—Orbicular.
- *Petal margin*.—Entire.
- *Petal arrangement*.—4 petals fused in a single whorl.
- *Petal number*.—4 petals.
- *Petal appearance*.—Matte.
- *Petal texture*.—Smooth, glabrous all surfaces.

Color:
- *Upper surface at first opening*.—Near Violet group RHS 85D.
- *Upper surface at maturity*.—Near Violet group RHS 85A, in cooler climates the color is darker Near Violet group RHS 86C.
- *Upper surface at fading*.—Near Violet group RHS 85C.
- *Under surface at first opening*.—Near Violet group RHS 85C.

*Under surface at maturity*.—Near Purple-violet group RHS N82C.
*Under surface at fading*.—Near Purple-violet group RHS N82C.

Petaloids or other floral structures: Not present.

Sepal:
*Number*.—4.
*Sepal appearance*.—4 sepals.
*Sepal arrangement*.—4 sepals in a single whorl.
*Sepal length*.—Approximately 1 mm.
*Sepal width*.—Approximately 0.5 mm.
*Sepal shape*.—Elliptic.
*Base*.—Truncate.
*Apex shape*.—Acute.
*Margin*.—Entire.
*Color*.—Near Green group RHS 143B (In cooler climates expression of anthocyanin will appear).

Peduncle:
*Length*.—Approximately 3 cm.
*Diameter*.—Approximately 2 mm.
*Angle*.—Not relevant.
*Strength*.—Strong.
*Color*.—Near Yellow-green group RHS 144B.

Pedicel:
*Length*.—Approximately 1 cm.
*Diameter*.—Approximately 0.5 mm.
*Angle*.—Approximately 80-110 degrees.
*Color*.—Near Green group RHS 143A all surfaces.
*Strength*.—Flexible, moderately strong.

REPRODUCTIVE ORGANS

*Number of pistils per flower*.—1.
*Pistil length*.—Approximately less than 1 mm.
*Stigma shape*.—Rounded to broadly spreading.
*Stigma color*.—Near Yellow-green group RHS N144A.
*Style color*.—Near Green group RHS 143C.
*Style length*.—Approximately 1 mm.
*Ovary color*.—Near Green group RHS 143C.
*Stamens quantity*.—6 stamens.
*Stamen length*.—1.5 mm.
*Anther shape*.—Elliptic.
*Anther size*.—0.3 mm.
*Anther color*.—Near Yellow-orange group RHS 14A.
*Pollen color*.—Near Yellow-orange group RHS 14A.
*Pollen quantity*.—Moderate.

OTHER CHARACTERISTICS

Disease and pest resistance: Neither resistance nor susceptibility to the normal diseases and pests of *Lobularia* have been observed.

Drought tolerance and cold tolerance: Plants of the new *Lobularia* have been noted to have good tolerance at temperatures from 1° C. to 38° C. and also in rain and wind conditions.

Fruit/seed production: Color and Shape of Fruits and Seeds: The fruits and Seeds are elliptical and flat. The color of the mature seed is near Grey-brown group RHS N199B.

What is claimed is:

1. A new and distinct cultivar of *Lobularia* plant named 'DLOBU22' as herein illustrated and described.

* * * * *